(12) United States Patent
Simmerer et al.

(10) Patent No.: US 7,725,967 B2
(45) Date of Patent: Jun. 1, 2010

(54) PATIENT BED FOR TRANSPORTING AND/OR POSITIONING A PATIENT

(75) Inventors: Thomas Simmerer, Krummesse (DE); Joerg-Uwe Meyer, Ratzeburg (DE); Ryszard Kummerfeld, Travemuende (DE); Volker Schierschke, Luebeck (DE); Goetz Kullik, Luebeck (DE)

(73) Assignee: Dräger Medical AG & Co. KG, Lübeck (DE)

( * ) Notice: Subject to any disclaimer, the term of this patent is extended or adjusted under 35 U.S.C. 154(b) by 489 days.

(21) Appl. No.: 11/691,768

(22) Filed: Mar. 27, 2007

(65) Prior Publication Data
US 2007/0251007 A1 Nov. 1, 2007

(30) Foreign Application Priority Data
Apr. 28, 2006 (DE) .................. 10 2006 019 748

(51) Int. Cl.
*A61G 7/00* (2006.01)
(52) U.S. Cl. .................. 5/601; 5/81.1 R; 5/83.1
(58) Field of Classification Search ............ 5/81.1 R, 5/83.1, 601, 625
See application file for complete search history.

(56) References Cited
U.S. PATENT DOCUMENTS 3,648,305 A * 3/1972 Ersek ................ 378/180
4,092,748 A * 6/1978 Ewers ................ 5/85.1
5,771,513 A * 6/1998 Kirchgeorg et al. ....... 5/625
6,174,584 B1 * 1/2001 Keller et al. ............ 428/102
6,582,456 B1 * 6/2003 Hand et al. ............ 607/108
6,851,145 B2   2/2005 Smith et al.

FOREIGN PATENT DOCUMENTS

| CH | 362795 | 8/1962 |
|----|--------|--------|
| DE | 31 07 221 A1 | 9/1982 |
| DE | 295 04 212.5 | 6/1995 |
| DE | 195 01 225 A1 | 7/1996 |
| DE | 10243611 | 4/2004 |
| EP | 0 677 283 A1 | 10/1995 |
| WO | WO 98/16938 | 4/1998 |

* cited by examiner

*Primary Examiner*—Fredrick Conley
(74) *Attorney, Agent, or Firm*—McGlew and Tuttle, P.C.

(57) ABSTRACT

A patient bed is provided for transporting and/or positioning a patient. The patient bed has a bed area provided for receiving a patient. The patient bed is flexible at least in the bed area in such a way that the patient bed can be rolled up around a part of the patient bed. The patient bed has at least one transport mount for acting on by a transporter, and the patient bed is designed to be transported via the at least one transport mount when loaded with a patient. The patient bed has a plurality of reinforcing fibers, which are flexible and tension-proof, wherein each of the reinforcing fibers passes through the bed area and is operatively connected to at least one of the at least one transport mount in such a way that a force acting on the bed area can be transmitted at least partially to the at least one transport mount.

20 Claims, 3 Drawing Sheets

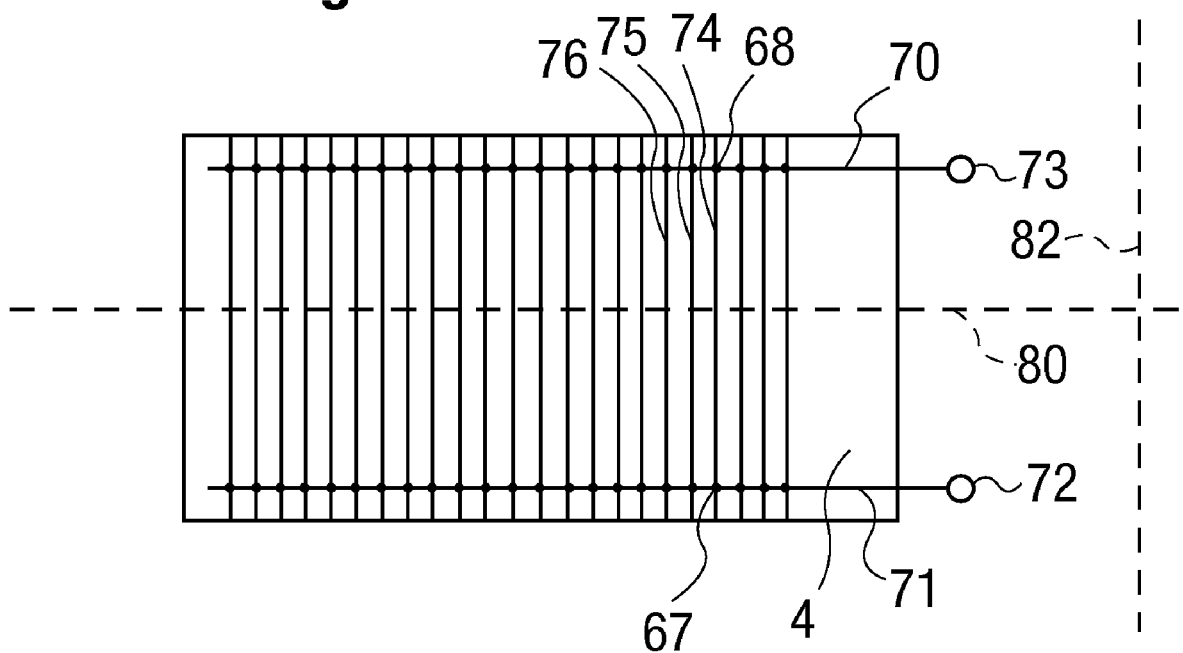

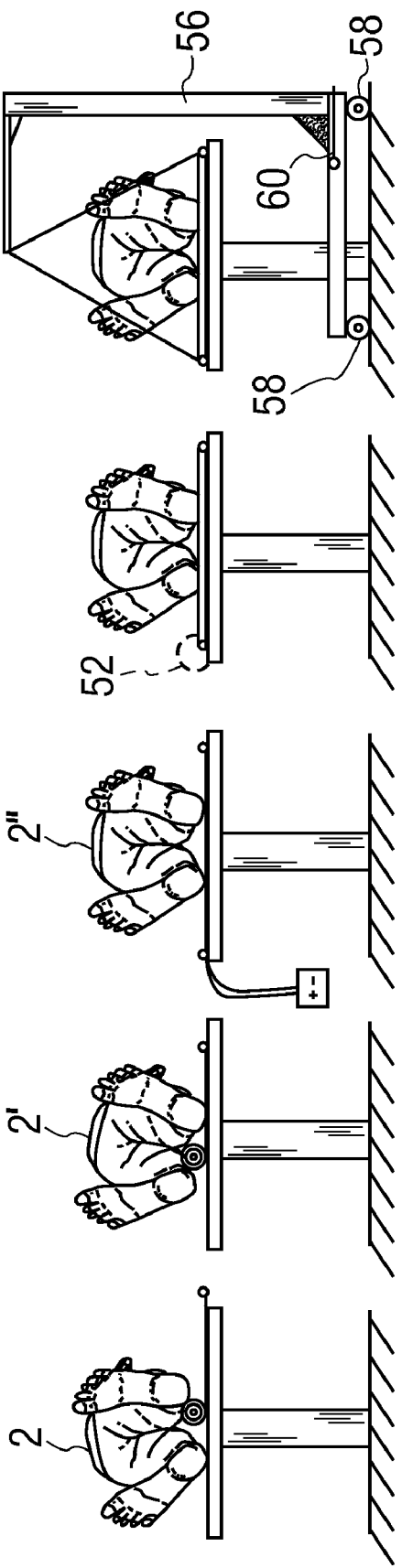

PATENT BED FOR TRANSPORTING AND/OR POSITIONING A PATIENT

CROSS REFERENCE TO RELATED APPLICATIONS

This application claims the benefit of priority under 35 U.S.C. §119 of German Patent Application DE 10 2006 019 748.8 filed Apr. 28, 2006, the entire contents of which are incorporated herein by reference.

FIELD OF THE INVENTION

The present invention pertains to a patient bed for transporting and/or positioning a patient.

BACKGROUND OF THE INVENTION

Positioning forms that are different from one another depending on the type of care are needed for the medical care of patients. The usual positioning forms are the hospital bed, medical stretchers and transport carts for initial medical care, an operating table or special beds for imaging examinations as well as nuclear spin tomography (magnetic resonance tomography (MRT)) in order to meet the special needs of a respective therapy or diagnostic procedure.

It has been necessary up to now to transport a patient from one bed to another bed. This transport method is particularly difficult for immobile or heavyweight or overweight patients, since up to now often no mechanical aids can be utilized as a result of space-related marginal conditions. The nursing staff is particularly burdened in these situations.

A grip sheet for hospitals and home nursing, with which a patient can be repositioned, has become known from DE 195 01 225 A1. Cotton, nonwoven fabrics or sailcloth are mentioned as materials for such a grip sheet.

A device for transporting a patient, which has a frame consisting of two longitudinal bars and cross bars connected to the longitudinal bars, has become known from DE 31 07 221 A1. Netted webs, lying above one another in a cross-like manner with overhanging ends, are fastened to these bars.

SUMMARY OF THE INVENTION

The basic problem of the present invention is that transport or positioning devices known from the state of the art are not suitable for a harsh clinical operation and particularly high hygienic requirements on disinfectability and simple handling of the device, as well as durability of the materials.

This problem is solved according to the present invention by a patient bed for transporting and/or positioning a patient, wherein the patient bed has a bed area provided for receiving a patient. The patient bed is designed as being flexible at least in the bed area in such a way that the patient bed can be rolled up around a part of the patient bed. The patient bed has at least one transport mount for acting on by a transporter, wherein the patient bed is designed to be transported via the at least one transport mount when loaded with a patient. The patient bed has a plurality of reinforcing fibers, which are designed as being flexible and tension-proof, wherein each of the reinforcing fibers passes through the bed area and is operatively connected to at least one of the at least one transport mount in such a way that a force acting on the bed area can be transmitted at least partially to the at least one transport mount.

In an advantageous embodiment variant of the patient bed—e.g., with a longitudinal dimension and a lateral dimension running at right angles thereto—the reinforcing fibers preferably run in a lateral direction with at least one direction component and indirectly connect at least two transport mounts lying opposite one another, wherein the transport mounts lying opposite one another include the bed area between them.

As an alternative to this, the reinforcing fibers may also be operatively connected to exactly one transport mount via a support structure. Such a support structure may enclose, for example, the bed area at least partially in a plane formed by the patient bed.

A patient bed with a longitudinal dimension and a lateral dimension preferably has a plurality of longitudinally directed reinforcing fibers.

Furthermore, a patient bed with a longitudinal dimension and a lateral dimension preferably has a plurality of laterally directed reinforcing fibers.

A patient bed with a longitudinal dimension and a lateral dimension especially preferably has a plurality of longitudinally directed reinforcing fibers and those laterally directed thereto.

A lateral dimension is preferably half of a longitudinal dimension; furthermore, a lateral dimension is preferably one meter. Consequently, the patient bed may advantageously be used on an actual patient bed.

A patient bed may have a plurality of reinforcing fibers, which are advantageously longitudinally directed with at least one direction component. Consequently, a reinforcing fiber may be woven into a fabric of a patient bed at right angles to a longitudinal direction and transmit a part of a force acting longitudinally in the fabric onto a transport mount.

A preferred embodiment of a patient bed has wheels looped around at least in the longitudinal direction, each of which forms a transport mount. A longitudinal bar for transporting the patient bed can be inserted into such a formed transport mount.

Furthermore, the patient bed preferably has looped-around edges in the lateral direction, each of which forms a transport mount. A crossbar for transporting the patient bed can be inserted into such a formed transport mount.

A longitudinal bar or a crossbar may itself each form a transport mount.

A longitudinal bar and/or a crossbar may advantageously each have a round cross section. Furthermore, the longitudinal bar or the crossbar or both may each have a smaller diameter along a bar longitudinal axis in the area of an end than in the area of the center.

A patient bed preferably has a support structure designed as being separable from the patient bed. Furthermore, the support structure is preferably designed to produce a natural stability at least in an edge area of the patient bed.

Furthermore, the support structure is preferably formed by longitudinal bars, and especially preferably by longitudinal bars and crossbars. Such a support structure is especially resistant to bending or resistant to pressure or resistant to buckling or a combination of these.

In a preferred embodiment of the patient bed, the reinforcing fibers each contain high-performance polyethylene (HPPE), extended-chain polyethylene (ECPE), carbon fibers, polyamide or polyester or a combination of these materials.

A reinforcing fiber, containing polyamide, preferably has a tensile strength of 0.7-1 KN per $mm^2$.

A polyester-containing reinforcing fiber preferably has a tensile strength of up to 0.85-13 KN per $mm^2$.

A carbon fiber-containing reinforcing fiber, and particularly an aramide reinforcing fiber, has a high tensile strength of preferably 2.5-4.5 KN per $mm^2$.

A reinforcing fiber, containing HPPE or ECPE, preferably has a tensile strength of 2.5-3.0 KN per mm$^2$.

A reinforcing fiber is preferably formed by a bundle of single reinforcing fibers.

In an advantageous embodiment, the patient bed contains a material that is not irritating to the skin, which is permeable to water vapor or inhibits bedsores or both at least in the bed area. Exemplary embodiments for such a material that is not irritating to the skin are cotton, linen, polyamide or a combination of these.

A bedsore-inhibiting patient bed is preferably designed as being sporicidal and contains, for example, silver. The silver may be vapor deposited onto a fiber. A portion of the silver of a patient bed is preferably selected in such a way that the patient bed does not or does not essentially compromise the detection of patients with an x-ray device, a computed tomography device or a magnetic resonance tomography device.

A patient bed may contain a fabric. The fabric of a patient bed may contain cotton, linen, polyamide or polyester.

Independently of a fabric or in addition to a fabric, a patient bed may contain a film, for example, a polypropylene film, a polyethylene film or a polyamide film. Such a patient bed with a film is advantageously waterproof.

A water-vapor-permeable patient bed with a film may advantageously be perforated.

A waterproof or water-repellent patient bed may also be coated or vapor-deposited with a water-repellent material.

In a preferred embodiment, the patient bed has an electrical heating element, which is designed to generate heat and to release same in the bed area.

For example, patients, who have experienced a state of shock, can advantageously be heated by a patient bed with a heating element.

An electrical heating element may be formed, for example, by carbon fibers or may contain carbon fibers. As an alternative to this, a heating element may be designed as a thin-layer heating element, wherein, in a thin-layer heating element, a film or a foil of electrically conductive material is vapor-deposited or lamninated onto a substrate.

A substrate may be formed by an electrically nonconductive film, for example, a polyethylene film, a polypropylene film or a polycarbonate film.

As an alternative to this, a heating element may also be formed by an electrically conductive metal wire. The electrically conductive metal wire may be a metal alloy.

In an advantageous embodiment of the patient bed, the electrical heating element is at least partially formed by reinforcing fibers, wherein the reinforcing fibers are designed for heating. As a result, a lower production cost is made possible. Thus, the reinforcing fibers have a dual function.

A patient bed may have a plurality of heating elements, which are to be connected electrically in parallel to one another, each of which is formed by reinforcing fibers connected electrically in series to one another.

Independently of this embodiment, reinforcing fibers in a bed area may together form a heating element, in which the reinforcing fibers are electrically connected in parallel to one another, and preferably via identical linear sections. For this purpose, a patient bed may have two electrically conductive connecting bars, each of which is electrically connected to the reinforcing fibers, which are electrically conductive and designed for heating, in such a way that the electrically conductive connecting bars enclose reinforcing fiber sections between them and each is connected to a reinforcing fiber section end in such a way that the reinforcing fiber sections are electrically connected in parallel to one another.

In a preferred embodiment, the patient bed has at least one temperature sensor. The temperature sensor is arranged and designed in such a way as to detect a temperature in the area of the bed and to produce a temperature signal corresponding to the detected temperature.

As an alternative to this, a temperature sensor may change its electrical properties depending on the detected temperature. A temperature sensor generating a temperature signal may be formed, for example, by a thermocouple pair. The thermocouple pair may generate a thermoelectric voltage depending on a difference in temperature.

A patient bed preferably has a temperature sensor that is formed by a thin layer of platinum. Such a platinum temperature sensor advantageously has a linear dependence of its electrical resistance on a temperature.

A temperature sensor may also be designed as a semiconductor temperature sensor and may contain silicon or barium titanate. In another embodiment of a temperature sensor for a patient bed, a temperature sensor is embodied as an NTC (Negative Temperature Coefficient) temperature sensor and has metal oxides. A temperature of the patient bed can be monitored by a temperature sensor, such that a patient cannot suffer any injury, for example, burns.

In an advantageous embodiment of the patient bed, the temperature sensor is formed by the electrical heating element itself. In this embodiment, the electrical heating element is connected, for example, to a control unit, which is designed to control the heating element with regard to time in heating intervals, wherein a heating break follows a heating interval. Furthermore, the control unit is designed to detect an electrical property of the heating element in a heating break. For example, such an electrical property is an ohmic resistance. Furthermore, the control unit is designed to change a temporal duration of the time interval depending on the ohmic resistance detected.

In this way, the heating element in this embodiment may advantageously be used as a temperature sensor as well.

In a preferred embodiment, the patient bed is radiolucent at least in the bed area at right angles to the bed. Such a radiolucent patient bed is free from radiopaque materials at least in the bed area. A patient bed advantageously has no or essentially no disturbing effect during the detection of a patient through the bed area in imaging procedures, such as computed tomography (CT), (MRT), positron emission tomography (PET) or single photon emission computed tomography (SPECT). In a radiolucent patient bed, an electrical heating element itself is designed as being radiolucent and contains, for example, carbon fibers.

A patient bed may advantageously be formed by at least two consecutive layers at right angles to the bed area, wherein the reinforcing fibers are arranged in a support layer provided for loading a patient.

Such a patient bed with at least two layers may also have, besides a support layer, a layer which is not irritating to the skin. In another advantageous embodiment of the patient bed, the patient bed contains a heating layer that is different from the support layer, wherein the heating layer contains the at least one heating element. For example, the support layer is formed by a fabric. A heating layer may advantageously contain a heat-conductive and/or heat-storing material. Consequently, a too intense, partial heating in the bed area can advantageously be prevented.

In an advantageous embodiment, a heating layer and a support layer are connected to one another in a separable manner. A patient bed with a support layer and a heating layer connected in a separable manner to the support layer may, for example, have push buttons or a zipper, wherein the support layer and the heating layer are connected in a separable manner to one another via the push buttons or the zipper in case of a zipper.

The present invention also pertains to a patient transport system with a patient bed of the above-described type and a transport crane. The transport crane is designed to engage with at least one of the at least one transport mounts or to act on same and to lift the patient bed. A transport crane preferably has a hydraulic device, which is operatively connected to a gripper for engaging or acting on the transport mounts.

The present invention is now described below on the basis of figures and the exemplary embodiments given with regard to the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 2 is a schematic view showing a patient bed with heatable reinforcing fibers according to the invention;

FIG. 3a is a view showing a stage of an exemplary application of a patient bed at a patient;

FIG. 3b is a view showing another stage of an exemplary application of a patient bed at a patient;

FIG. 3c is a view showing another stage of an exemplary application of a patient bed at a patient;

FIG. 3d is a view showing another stage of an exemplary application of a patient bed at a patient;

FIG. 3e is a view showing another stage of an exemplary application of a patient bed with a transporter;

FIG. 4 is an enlarged view of a corner connection shown in FIG. 3d;

FIG. 5 is a top view showing an exemplary embodiment of a patient bed with handles; and FIG. 6 is an enlarged view of a corner connection shown in FIG. 5.

DESCRIPTION OF THE PREFERRED EMBODIMENTS

Figure 1:
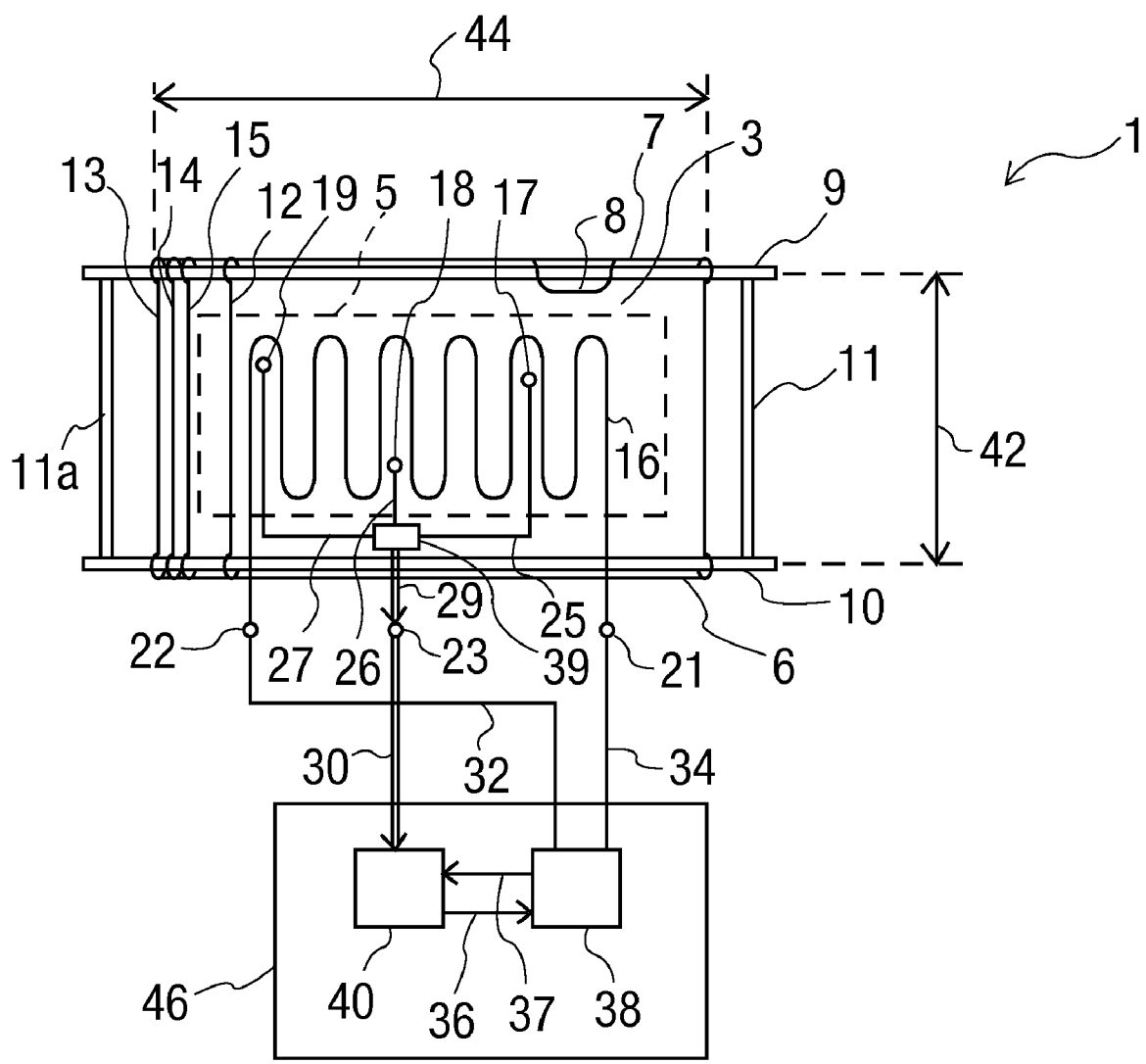
FIG. 1 is a schematic view of a patient bed according to the invention.

Referring to the drawings in particular, FIG. 1 shows a patient bed 1. The patient bed 1 has a cloth 3, in which a bed area 5 is provided for receiving a patient (not shown in this FIG. 1).

The cloth 3 is formed, for example, by a fabric that is not irritating to the skin, which may contain, for example, cotton, linen or polyester or polyamide or a combination of these materials.

The cloth 3 has a plurality of reinforcing fibers, of which the reinforcing fibers 12, 13, 14 and 15 are shown as examples.

The reinforcing fiber 12 passes though, for example, the bed area 5.

The cloth 3 contains a plurality of reinforcing fibers (not shown in this figure), which extend over the bed area 5 and which pass though the bed area 5.

The cloth 3 of the patient bed 1 is looped around in the area of an edge 7 and thus forms a tube in the area of the edge 7, in which [tube] a transport bar 9 can be pushed over the longitudinal dimension 44 of the patient bed 1 along the longitudinal direction.

A recess 8, which extends at right angles to a longitudinal direction along the longitudinal dimension 44 is also shown, for example, such that a hand of an adult human transporter may grip in there and may lift the transport bed 1.

A patient bed 1 may have a plurality of such recesses as recess 8.

The transport bed 1 has a lateral dimension 42 that is half of the longitudinal dimension 44. The patient bed 1 thus has a rectangular shape.

The patient bed 1 has an edge 6 running in the longitudinal direction, which lies opposite the edge 7, such that the bed area 5 is enclosed between edge 6 and edge 7. The cloth 3 is looped around in the area of the edge 6, such that a transport bar 10 can be pushed through a looped tunnel thus formed in the longitudinal direction. The transport bar 10 and the transport bar 9 are each connected by a crossbar 11 in the area of an end and are connected by a crossbar 11a in the area of an end opposite to this [end]. The transport bars 9 and 10 together with the crossbars 11 and 11a form a support structure, which is designed to lift the patient bed 1 together with a patient.

The patient bed 1 also has a heating element 16, which is arranged in the bed area 5 and is connected to the cloth 3. The heating element 16 may be sewn, woven or laminated into the cloth 3. For example, the cloth 3 of the patient bed 1 may have a two-layer design, wherein the heating element 16 is arranged between these two layers, at right angles to the patient bed. The heating element 16 may be designed as a wire-like or as a thin-layer heating element.

The patient bed 1 also has a plurality of temperature sensors, of which the temperature sensors 17, 18 and 19 are shown as examples. The temperature sensor 17 is connected to an interface 39 via a connecting line 25, the temperature sensor 18 is connected to the interface 39 via a connecting line 26 and the temperature sensor 19 is connected to the interface 39 via a connecting line 27. The temperature sensors 17, 18 and 19 are each designed to detect a temperature and to change their electrical resistance depending on the temperature detected. The interface 39 is designed to generate a temperature signal, which represents the temperatures detected by the temperature sensors 17, 18 and 19, and to make this [signal] available via a data bus 29 at a terminal 23.

The patient bed also has a control unit 46. The control unit 46 has a regulating unit 40 and a heating control unit 38. The heating control unit 38 is connected to the heating element 16 via a connecting line 34 and via a terminal 21 and to the heating element 16 via a connecting line 32 and a terminal 22.

The heating control unit 38 has an input for a control signal, wherein the input for the control signal is connected to the regulating unit 40 via a connecting line 36. The heating control unit 38 is designed, depending on a control signal received via the connecting line 36 on the input side, to send an electrical current for operating the heating element 16 via the connecting lines 34 and 32 on the output side.

On the input side, the regulating unit 40 is connected to the terminal 23 via a data bus 30 and thus indirectly to the temperature sensors 17, 18 and 19. The regulating unit 40 may generate the control signal depending on the temperature signal received at the data bus 30 and send the control signal on the output side via the connecting line 36. For example, the regulating unit 40 may be a PI (proportional-integral) regulating unit, which is designed to generate the control signal to be sent on the output side depending on an input signal received on the input side according to a predetermined assignment procedure. In case of a PI regulating unit, the predetermined assignment procedure has a proportional and integral component.

In this exemplary embodiment, the heating control unit is connected to the regulating unit 40 via a connecting line 37 and is designed to detect an electrical resistance connected between the terminals 21 and 22 and to generate a resistance signal corresponding to the electrical resistance detected and to transmit this [signal] to the regulating unit 40 on the output side via the connecting line 37.

The regulating unit 40 may generate the control signal depending on the resistance signal received via the connecting line 37. For example, the regulating unit 40 may not generate a control signal or may generate a switch-off signal in the case of a predetermined too-high resistance value, which is represented by the resistance signal. Thus, in case of a defect of the heating element 16, which, for example, is caused by a fold of or damage to the heating element 16, the regulating unit 40 may switch off the heating element and thus offer protection against local overheating at the defective point.

A patient bed 1 may have the above-described elements without the control unit 46.

FIG. 2 shows—schematically and independently of the cloth 3 shown in FIG. 1—another exemplary embodiment for a cloth of a patient bed 1 shown in FIG. 1. The cloth 4 has a plurality of heatable reinforcing fibers, of which the heatable reinforcing fibers 74, 75 and 76 are shown as examples, arranged at right angles to a longitudinal axis 80.

The cloth 4 has an electrical current supply 70 and an electrical current supply 71, each of which is designed as a conduction system and each of which runs parallel to the longitudinal axis 80.

Each of the heatable reinforcing fibers is connected to the electrical current supply 70 via a first electrical connection and connected to the electrical current supply 71 via a second electrical connection along a lateral axis 82—at a distance from the first electrical connection. Consequently, electrical heating sections are formed on each of the heatable reinforcing fibers, wherein the electrically conductive sections are each electrically connected in parallel to one another.

A first electrical connection 68 and a second electrical connection 67 are shown as connecting nodes as examples.

The electrical current supply 70 is connected to an electrical terminal 73, and the electrical current supply 71 is connected to an electrical terminal 72. The electrical terminal 73 is provided for connecting to a control unit 46 shown in FIG. 1 and there for connecting to the connecting line 34. The electrical terminal 72 is provided for connecting to the control unit 46 and there to the connecting line 32. The heating element 16 may be omitted in this exemplary embodiment.

An electrical resistance of the heating element formed by the reinforcing fiber sections may be detected by the heating control unit 38 shown in FIG. 1 and a resistance signal corresponding to the electrical resistance may be generated and may be transmitted via the connecting line 37 to the regulating unit 40 shown in FIG. 1.

The heating element formed by the reinforcing fiber sections may be supplied with current via the electrical terminals 72 and 73.

FIGS. 3a, 3b, 3c, 3d and 3e schematically show an exemplary application for using the patient bed 1 shown in FIG. 1.

FIG. 3a schematically shows a first step for using the patient bed 1. An examination table 50, for example, in a so-called "shock room" of a hospital, which is provided for initial medical care, is shown. The patient 2 lies on his back; the bottoms of his feet, his legs and parts of his abdomen can be seen. The patient bed 1 is fixed at a longitudinal bar—also called transport bar 9 below, wherein the transport bar 9 is inserted, beforehand, into a transport mount designed as a tubular, longitudinal loop. Then, the patient bed 1 can be partially unwound under the patient 2 who is rolled onto a first side slightly about his longitudinal axis.

FIG. 3b shows the patient 2', who is rolled about his longitudinal axis to a second side opposite the first side and, consequently, in a next step, the still partially wound-up patient bed 1 located under his body can be unwound.

FIG. 3c schematically shows the patient bed 1 now unwound flat on the examination table 50 with the inserted transport bar and the inserted transport bar 10. Also shown is the control unit shown in FIG. 1, which is connected to the transport bed 1 via the connecting lines 32 and 34 and to the heating element 16 (not shown in this view). The patient 2" can now be heated via the heating surface 16.

FIG. 3d shows the patient bed 1, wherein the transport bar 9 and the transport bar 10 are connected to one another via a transport bar 11 shown in FIG. 1 and via a crossbar 11a shown in FIG. 1.

FIG. 3e shows a transport crane 56 with wheels 58 of a patient transport system comprising the transport crane and a patient bed, wherein the transport crane is designed to act on the patient bed 1 at transport mounts provided for lifting and to lift the patient bed 1 together with a patient.

In this exemplary embodiment, the transport crane 56 is connected to the patient bed 1 via four cables and there to this patient bed at each of the corners. The transport crane 56 has a foot pump (not shown), which is operatively connected to a working cylinder (not shown), and wherein the foot pump is connected to a foot lever 60 and can be operated by the foot lever 60.

FIG. 4 shows a detailed view of a corner connection 52 shown in FIG. 3d. A section in the area of an end of the crossbar 11, which is connected in the area of an end of the transport bar 10 to the transport bar 10 via a safety clamp 54, is shown.

The crossbars 11 and 11a each have ends designed for connecting to a longitudinal bar. The end areas of the crossbars have semicylinder-shaped recesses for this, such that an end of a crossbar can be fastened to a longitudinal bar in a positive locking manner, at right angles to the longitudinal direction of the longitudinal bar.

FIG. 5 shows a view of a patient bed 1, which is loaded with a patient. A corner connection 53 is shown in a detailed, sectional view in FIG. 6.

FIG. 6 shows a detailed sectional view of the corner connection 53 shown in FIG. 5. A section is shown with an end of the crossbar 11 and a section with an end of the transport bar 10, each of which are inserted into the patient bed 1.

Differently and independently of the patient bed shown in FIG. 1, the patient bed shown in FIG. 5 and in FIG. 6 has a cloth, which is additionally looped around in the area of the cross bar 11, such that the cross bar 11 can be inserted into the tube formed by the looping around. The cloth is correspondingly looped around on an opposite side of the cross bar 11 along the longitudinal axis, such that the cross bar 11a (not shown in this FIG. 6) can be inserted into the tube thus formed.

In this exemplary embodiment, the patient bed additionally has reinforcing fibers 62 running in the longitudinal direction. Each of the reinforcing fibers 62 is operatively connected to the crossbar 11 and to the crossbar 11a in such a way that a force acting on the bed area can be at least partially transmitted to the transport mounts, and especially to the tubes and from there to the crossbars as part of a support structure. Also shown are reinforcing fibers 64, which run at right angles to the longitudinal direction of the patient bed and are arranged and designed corresponding to the reinforcing fibers 13, 14 and 15 shown in FIG. 1.

Also shown is a carrying handle 66, which is connected in a separable manner to the transport bar 10 in the area of an opening (not shown in this figure) in the looped edge area of the cloth. The carrying handle 66 thus forms another transport mount for manually transporting the patient bed.

While specific embodiments of the invention have been shown and described in detail to illustrate the application of the principles of the invention, it will be understood that the invention may be embodied otherwise without departing from such principles.

What is claimed is:

1. A patient bed for transporting and/or positioning a patient, the patient bed comprising:
    a bed area part provided for receiving a patient, said bed area part being flexible, said bed area part being rolled up around at least a portion of itself in a rolled up state;
    a transporter;
    a first transport bar comprising a first transport mount for acting on by said transporter
    a second transport bar comprising a second transport mount for acting on by said transporter, said bed area part being transported via said first transport bar and said second transport bar when loaded with a patient;
    a plurality of reinforcing fibers, said reinforcing fibers being flexible and tension-proof, each of said reinforcing fibers passing through said bed area part and being operatively connected to said first transport bar in said rolled up state, said bed area part being movable such that said bed area part moves from said rolled up state to an extended state, said plurality of reinforcing fibers being operatively connected to said first transport bar and said second transport bar in said extended state such that a force acting on said bed area part can be transmitted at least partially to said first transport bar and said second transport bar, said bed part area and said plurality of reinforcing fibers forming a supportive structure in said extended state, said bed part area and said plurality of reinforcing fibers forming a flexible structure in said rolled up state.

2. A patient bed in accordance with claim 1, further comprising: an electrical heating element designed to produce heat and to release same in a region of said bed area part.

3. A patient bed in accordance with claim 2, wherein said electrical heating element is formed at least partially by heating said reinforcing fibers.

4. A patient bed in accordance with claim 1, further comprising: a temperature sensor arranged and designed to detect a temperature in a region of said bed area part and to generate a temperature signal which corresponds to the detected temperature or to change an electrical property depending on the detected temperature.

5. A patient bed in accordance with claim 4, further comprising: an electrical heating element designed to produce heat and to release same in a region of said bed area part wherein said temperature sensor is formed by said electrical heating element.

6. A patient bed in accordance with claim 1, wherein said patient bed is radiolucent at least in the area of the bed at right angles to the bed and/or has no or essentially no disturbing effect when detecting a patient throughout the bed area in imaging procedures, such as computed tomography, magnetic resonance tomography, positron emission tomography or single photon emission computed tomography.

7. A patient bed in accordance with claim 1, wherein said bed area part comprises at least two consecutive layers at right angles to the patient bed, wherein said reinforcing fibers are arranged in a support layer provided for loading a patient.

8. A patient bed in accordance with claim 7, wherein the patient bed contains a heating layer that is different from the support layer, wherein the heating layer contains at least one heating element.

9. A patient bed in accordance with claim 1, wherein said bed area part comprises a material that is not irritating to the skin, which is permeable to water vapor and/or inhibits bedsores.

10. A patient bed in accordance with claim 1, wherein said reinforcing fibers comprise one or more of high-performance polyethylene, extended-chain polyethylene, carbon fibers, polyamide and polyester.

11. A patient bed in accordance with claim 1, further comprising a first crossbar and a second crossbar, said first crossbar and said second crossbar being detachably connected to said first transport bar and said second transport bar, said first crossbar, said second crossbar, said first transport bar and said second transport bar defining a support structure, said support structure providing a natural stability of the patient bed at least in one edge area of the patient bed.

12. A patient transport system, comprising:
    a bed area part provided for receiving a patient, said bed area part being flexible whereby said bed area part is rolled up around at least a portion of itself in a rolled up position;
    a transport mounting arrangement comprising at least a first support structure comprising a first transport mount and a second support structure comprising a second transport mount for acting on by a transporter, the patient bed being transported via said first transport mount and said second transport mount when loaded with a patient;
    a plurality of reinforcing fibers, said reinforcing fibers being flexible and tension-proof, each of said reinforcing fibers passing through said bed area part and being operatively connected to said first support structure in said rolled up position, each of said plurality of reinforcing fibers being rolled up around at least a portion of itself in said rolled up position, said bed area part and said plurality of reinforcing fibers being movable from said rolled up position to an extended position, each of said reinforcing fibers being operatively connected to said first support structure and said second support structure in said extended position such that a force acting on said bed area part can be transmitted at least partially to said first support structure and said second support structure, said plurality of reinforcing fibers and said bed area part being in a flattened configuration in said extended state.

13. A system according to claim 12, wherein said transporter is a transport crane designed to engage with said transport mount or to act on same and to lift said bed area part.

14. A system according to claim 12, wherein said transport mounting arrangement comprises a first crossbar and a second crossbar, said first crossbar and said second crossbar being detachably connected to said first transport bar and said second transport bar in said extended state to define a support structure, said support structure providing a natural stability of the patient bed at least in one edge area of the patient bed.

15. A system in accordance with claim 12, wherein said bed area part comprises a material that is not irritating to the skin, which is permeable to water vapor, said reinforcing fibers comprising one or more of high-performance polyethylene, extended-chain polyethylene, carbon fibers, polyamide and polyester.

16. A system in accordance with claim 12, further comprising: an electrical heating element designed to produce heat and to release same in a region of said bed area part, said electrical heating element comprising an element disposed in or adjacent to said fibers or said bed area part or being formed by heating reinforcing fibers disposed in or adjacent to said fibers or said bed area part.

17. A patient bed for transporting and/or positioning a patient, the patient bed comprising:
   a bed area part provided for receiving a patient, said bed area part comprising a flexible material that is not irritating to the skin, which is permeable to water vapor, said flexible material being rolled up around at least a portion of itself to define a rolled up state;
   a transport mounting arrangement comprising a first support structure and a second support structure, said first support structure and said second support structure having at least one transport mount for acting on by a transporter, the patient bed being transported via said transport mount of said first support structure and said transport mount of said second support structure when loaded with a patient;
   a plurality ofreinforcing fibers, said reinforcing fibers being flexible and tension-proof, each of said reinforcing fibers supporting said bed area part and being operatively connected to said first support structure in said rolled up state, each of said plurality of reinforcing fibers being rolled up around at least a portion of itself in said rolled up state, said plurality of reinforcing fibers and said bed area part being movable such that said plurality of reinforcing fibers and said bed area part move from said rolled up state to an extended state, said plurality of reinforcing fibers being operatively connected to said first support structure and said second support structure such that a force acting on said bed area part can be transmitted at least partially to said first support structure and said second support structure, at least a portion of said bed area part having a rolled up bed area part thickness in said rolled up state, said bed area part having an extended thickness in said extended state, said bed area part thickness being greater than said extended thickness.

18. A patient bed according to claim 17, further comprising a transport crane forming the transporter, said transport crane engaging said transport mount or to act on same and to lift said bed area part.

19. A patient bed according to claim 18, wherein said transport mounting arrangement comprises a third support structure and a fourth support structure, said third support structure and said fourth support structure being detachably connected to said first support structure and said second support structure in said extended state, said first support structure, said second support structure, said third support structure and said fourth support structure providing a natural stability of the patient bed at least in one edge area of the patient bed.

20. A patient bed according to claim 19, further comprising:
   an electrical heating element designed to produce heat and to release same in a region of said bed area part, said electrical heating element comprising an element disposed in or adjacent to said fibers or said bed area part or being formed by heating reinforcing fibers disposed in or adjacent to said fibers or said bed area part; and
   a temperature sensor arranged and designed to detect a temperature in a region of said bed area part and to generate a temperature signal which corresponds to the detected temperature or to change an electrical property of said electrical heating element depending on the detected temperature.

* * * * *